United States Patent [19]
Oglesby, Jr.

[11] Patent Number: 5,339,120
[45] Date of Patent: Aug. 16, 1994

[54] RETINA EVALUATION RETICLE APPARATUS

[76] Inventor: Frank L. Oglesby, Jr., 1417 Plainview St., Kingsport, Tenn. 37664

[21] Appl. No.: 976,539

[22] Filed: Nov. 16, 1992

[51] Int. Cl.$^5$ .............................................. A61B 3/10
[52] U.S. Cl. .................................... 351/211; 351/206
[58] Field of Search ................ 351/214, 204, 211, 206

[56] References Cited

U.S. PATENT DOCUMENTS

| | | | |
|---|---|---|---|
| 4,196,980 | 4/1980 | Heine | 351/211 |
| 4,540,253 | 9/1985 | Hashika et al. | 351/211 |
| 4,900,143 | 2/1990 | Bessler et al. | 351/214 |
| 4,934,809 | 6/1990 | Volk | 351/214 |
| 5,046,836 | 9/1991 | Volk | 351/219 |
| 5,080,477 | 1/1992 | Adachi | 351/212 |
| 5,255,025 | 10/1993 | Volk | 351/205 |

*Primary Examiner*—Loha Ben
*Assistant Examiner*—Thomas Robbins
*Attorney, Agent, or Firm*—Malcolm G. Dunn

[57] ABSTRACT

A retina evaluation reticle apparatus for use in a slit lamp biomicroscope and removably positioned at the focusing point of the slit lamp biomicroscope and spaced therein from a patient to be examined, the retina evaluation reticle apparatus including a reticle defining and including thereacross a grid sized with reference to the expected diameter of an optic nerve for enabling measurements to be made from the optic nerve.

4 Claims, 2 Drawing Sheets

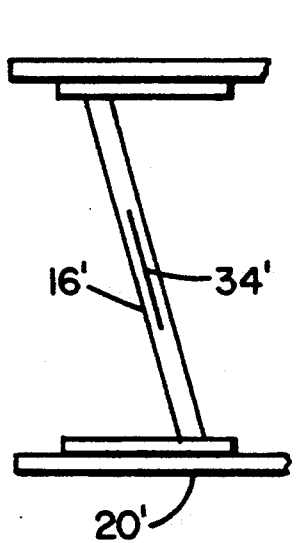
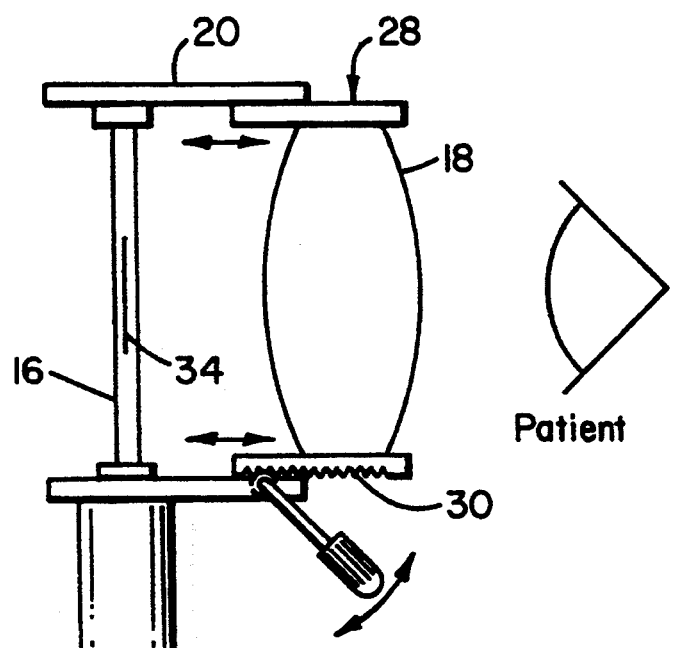
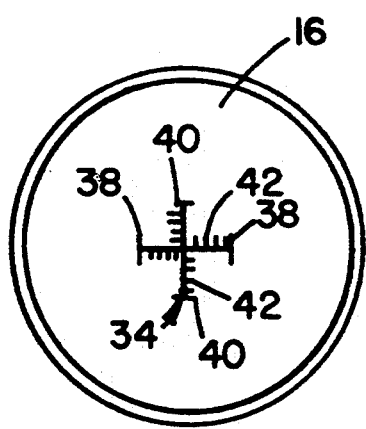
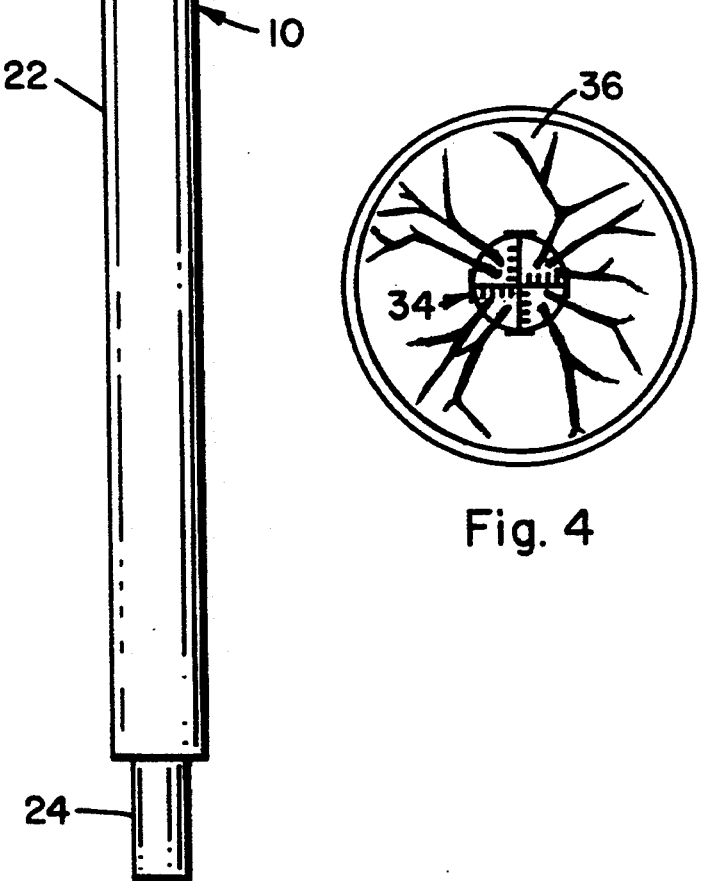
Fig. 5
Fig. 2
Fig. 3
Fig. 4

RETINA EVALUATION RETICLE APPARATUS

TECHNICAL FIELD

The present invention concerns an apparatus for indirect biomicroscopy of the eye for enabling measurements to be made from the optic nerve of a patient, and more particularly concerns a retina evaluation reticle apparatus employed within a slit lamp biomicroscope.

BACKGROUND OF THE INVENTION

Practitioners in the fields of ophthalmology and optometry often will use hand-held devices and the like to make an examination of the eye of the patient, such as disclosed in U.S. Pat. No. 5,046,836. U.S. Pat. No. 4,196,980 discloses in FIGS. 2 and 3 examination patterns 3' projected onto the retina of the eye, as another example of a hand-held device.

It is also known in the prior art that an ophthalmologist or optometrist may use mechanical devices for holding an examining lens relative to a patient's eye, such as one attached to a special headband worn by the examiner, so as to free his or her hands, perhaps for the purpose of holding the eyelid of the patient in position, or of moving other devices between the mechanical device being held and the eye of the patient, such as shown in FIG. 3 of U.S. Pat. No. 4,900,143.

It is further known to attach holders to the head rest of a slit lamp biomicroscope relative to the location of the eyes of the patient. U.S. Pat. No. 4,934,809, for instance, discloses a lens positioning device, which is attached to one of the chin rest vertical bars of a slit lamp biomicroscope and includes a plurality of movable arms for positioning a lens relative to the eye of the patient.

SUMMARY OF THE INVENTION

The present invention concerns a retina evaluation reticle apparatus for use in and for removably positioning at the focusing point of a slit lamp biomicroscope and spaced in the slit lamp biomicroscope from a patient to be examined. The retina evaluation reticle apparatus includes a reticle defining and including thereacross a grid sized with reference to the expected average diameter of an optic nerve for enabling measurements to be made from the optic nerve of a patient during an indirect biomicroscopy of the eye.

The present invention more specifically concerns apparatus for indirect biomicroscopy of the eye comprising a reticle supported within a vertical plane at the focusing point of a slit lamp biomicroscope between and within the slit lamp biomicroscope and a patient to be examined, the reticle defining and including thereacross a grid for enabling the operator to make measurements from the optic nerve of the patient, and a condensing lens coaxially spaced from the reticle toward the patient and having opposite faces that are located in two vertical planes.

The condensing lens is adjustable coaxially toward and away from the reticle for focusing an aerial image of the retina of the patient on the grid, and an arrangement is provided for making such adjustment.

An arrangement is also provided for removably positioning and supporting the reticle and the condensing lens, the arrangement comprising a vertical support positioned at the focusing point of the slit lamp biomicroscope and being located perpendicular to the optical axis of the slit lamp biomicroscope between the biomicroscope and the patient to be examined.

In an alternate embodiment, the reticle and its defined and included grids may be inclined at an angle of about 4 degrees to about 8 degrees with respect to the vertical plane at the focusing point of the slit lamp biomicroscope.

BRIEF DESCRIPTION OF THE DRAWINGS

FIG. 2 is an elevational view of the retina evaluation reticle apparatus, partly in cross-section, and illustrating its locational relationship with respect to the eye of a patient;

FIG. 3 is a plan view of the reticle illustrating one form that a grid may take;

FIG. 4 is an illustrated view of an optic nerve and the grid, as may be seen through the apparatus of the invention in a slit lamp biomicroscope; and FIG. 5 is a fractional elevational view of an alternate embodiment showing the reticle inclined at an angle.

DESCRIPTION OF THE PREFERRED EMBODIMENT

Figure 1:
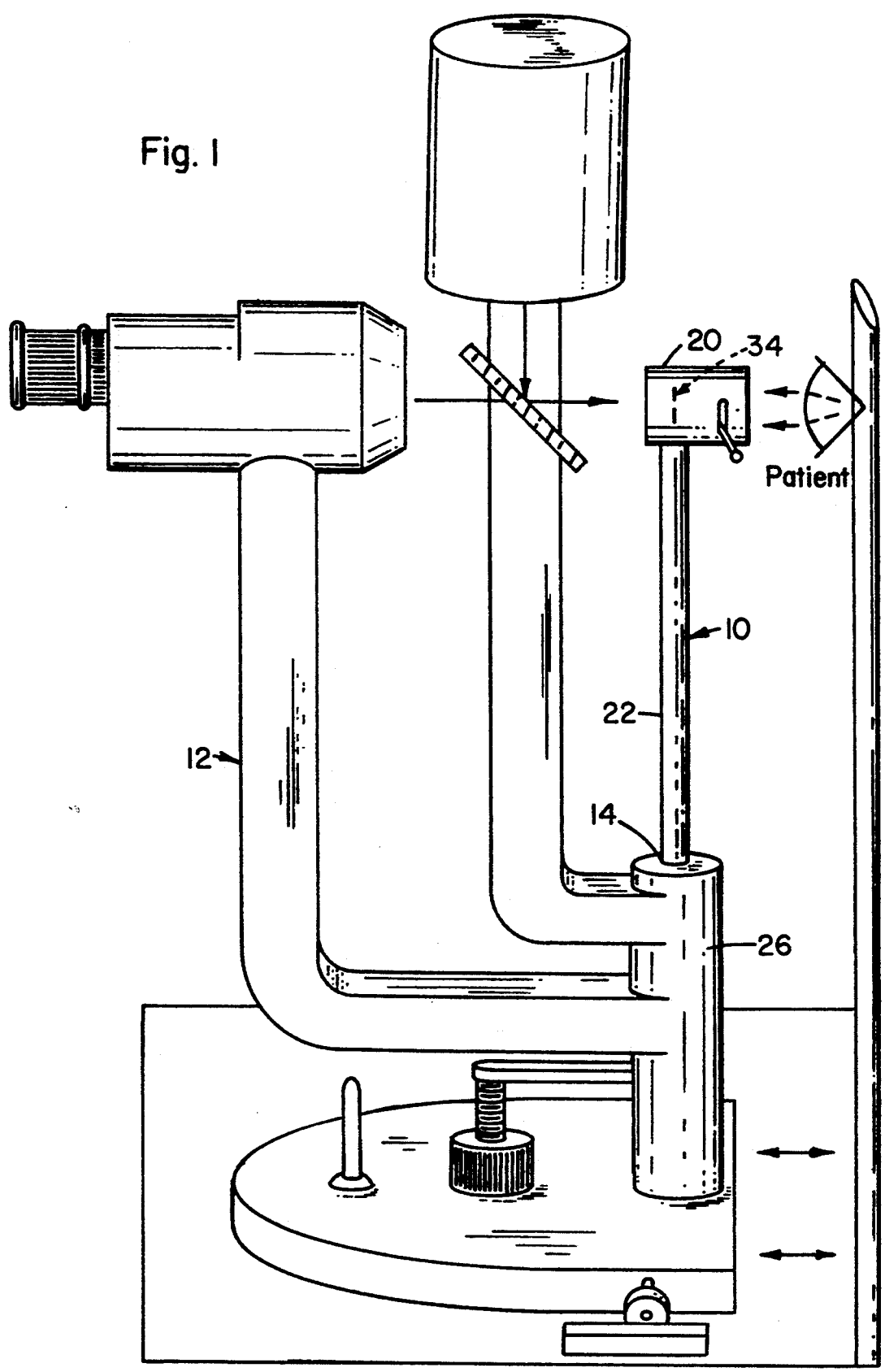
FIG. 1 illustrates an elevational view of the apparatus of the invention showing the retina evaluation reticle apparatus positioned at the focusing point of a slit lamp biomicroscope.

With reference to FIG. 1 of the drawings, the retina evaluation reticle apparatus is shown at 10 installed on a slit lamp biomicroscope 12 and seated within an aperture 14 on the slit lamp biomicroscope. The aperture is usually provided by the manufacturer of the slit lamp biomicroscope for insertion of a focusing rod (not shown) that is initially employed by the person using the slit lamp biomicroscope to regulate the focusing of the biomicroscope for his or her own particular refractive error.

With reference now also to FIG. 2, the retina evaluation reticle apparatus 10 comprises a reticle 16 and a condensing lens 18 coaxially adjustably spaced from the reticle. The reticle and the condensing lens are supported within a housing 20 that may be cylindrical in configuration. The housing along with the reticle and condensing lens are held at an appropriate position relative to the focusing point of the slit lamp biomicroscope 12 by a vertical support 22. The lower end portion 24 of the vertical support at the opposite end from the housing 20 is reduced in diameter so as to be inserted and securely seated within the aperture 14 provided in the columnar-like portion 26 of the slit lamp biomicroscope. It is to be noted that the axis of the vertical support 22 is also co-extensive with the focal plane of the slit lamp biomicroscope so that when the retina evaluation reticle apparatus 10 is attached, the slit lamp biomicroscope focuses at or within the reticle 16.

The condensing lens 18 is preferably supported within an encompassing annular collar 28 that is exteriorly provided on its lower side with a geared rack 30 so that by manually turning the finger-actuated pinion adjustment 32, the condensing lens may be coaxially adjustably moved closer to or farther away from the reticle 16. The condensing lens may preferably be a Volk 78 diopter condensing lens, which is manufactured by Volk of Mentor, Ohio.

The reticle 16 is in the form of a transparent support defining and including thereacross a grid 34, which is sized with reference to the expected average diameter of an optic nerve of a patient and dioptric power of the condensing lens employed. See, for instance, FIG. 4, which shows a view of an optic nerve 36 and the grid 34. The expected average diameter of an optic nerve will usually come within and between the overall diameter of the cross-bars 38, 40 of the grid 34. The cross bars are each preferably divided along their lengths at intervals by marks 42 intersecting at right angles thereto to facilitate making measurements. The transparent support of the reticle may be made of a suitable material, such as plastic or glass, so as to allow the passage of light therethrough from the slit lamp biomicroscope.

Although the grid 34 may be provided on one or the other of the exterior faces of the transparent support, it preferably is provided within the transparent support. In the latter manner, the reticle may be centrally located and its vertical axis will coincide with the axis of the vertical support 22. The grid itself is then positioned so as to be in the vertical plane of the focusing point of the slit lamp biomicroscope and of an aerial image of the patient's retina.

The purpose of the coaxial adjustment of the condensing lens 18 is to bring an aerial image of the patient's retina into focus on the grid of the reticle 16, and thus also at the focusing point of the slit lamp biomicroscope. The condensing lens is thus positioned between the patient and the reticle 16, while the reticle 16 is located between the operator of the slit lamp biomicroscope and the condensing lens.

The retina evaluation reticle apparatus 10 may be used to measure the cup disc ratio, for instance, or an indentation in the optic nerve of a patient. In this manner, the extent of optic nerve cupping and its progress may be evaluated from time to time. The apparatus may also be employed to inspect and make other measurements from the optic nerve. The average diameter of an optic nerve is generally about 1.5 millimeters.

In the operation of the retina evaluation reticle apparatus 10, the light source from the slit lamp biomicroscope 12 passes through the optical system of the slit lamp biomicroscope and then is projected through the reticle 16, including its defined grid 34, and the condensing lens 18 and into the patient's eye. Light reflected back through the condensing lens projects or superimposes an aerial image of the optic nerve 36 on the grid 34 at the focusing point of the slit lamp biomicroscope.

In FIG. 5, an alternate embodiment of the invention is shown. The reticle 16' and its defined and included grid 34' may be inclined at an angle, such as about 4 degrees to about 8 degrees with respect to the vertical plane of the focusing point of the slit lamp biomicroscope within the housing 20'. This is to avoid any undesired light reflections to the operator from the transparent support. The inclination of the reticle may be avoided by the use of a transparent support of suitable non-glare material, so long as there is no reduction in clarity of the view of the optic nerve by the operator.

The invention has been described in detail with particular reference to preferred embodiments thereof, but it will be understood that variations and modifications can be effected within the spirit and scope of the invention.

I claim:

1. A retina evaluation reticle apparatus and means for removably positioning said apparatus within a vertical plane at a focusing point of a slit lamp biomicroscope and spaced in said slit lamp biomicroscope from a patient to be examined, said retina evaluation reticle apparatus including a reticle defining and including thereacross a grid for enabling measurements to be made from the optic nerve of said patient during an indirect biomicroscopy of the eye, and a condensing lens coaxially spaced from said reticle toward said patient for forming an aerial image of said optic nerve upon said grid and having opposite faces that are located in two vertical planes, said grid being sized with reference to an expected average diameter of said optic nerve and a dioptric power of said condensing lens.

2. Apparatus for indirect biomicroscopy of the eye as defined in claim 1, and wherein said condensing lens is adjustable coaxially toward and away from said reticle for focusing said aerial image on said grid, and means is provided for adjusting said condensing lens.

3. Apparatus for indirect biomicroscopy of the eye as defined in claim 1, and wherein said means for removably positioning said apparatus comprises a vertical support positioned at the focusing point of said slit lamp biomicroscope and being located perpendicular to the optical axis of said slit lamp biomicroscope between said biomicroscope and said patient to be examined.

4. Apparatus for indirect biomicroscopy of the eye as defined in claim 1, and wherein said reticle is inclined at an angle from about 4 degrees to about 8 degrees with respect to said vertical plane.

* * * * *